United States Patent

Piskala et al.

[11] 3,954,752
[45] May 4, 1976

[54] PROCESS FOR PREPARING 2',3',5'-TRI-0-ACETYL-6-AZAURIDINE

[75] Inventors: Alois Piskala; Frantisek Sorm, both of Prague, Czechoslovakia

[73] Assignee: Ceskoslovenska akademie ved, Prague, Czechoslovakia

[22] Filed: June 5, 1974

[21] Appl. No.: 476,459

[30] Foreign Application Priority Data
June 6, 1973  Czechoslovakia.................. 4916-73

[52] U.S. Cl............................................ 260/248 AS
[51] Int. Cl.$^2$..................................... C07D 253/06
[58] Field of Search.............................. 260/248 AS

[56] References Cited
UNITED STATES PATENTS

| | | | |
|---|---|---|---|
| 3,352,849 | 11/1967 | Shen et al....................... | 260/248 X |
| 3,357,976 | 12/1967 | Restivo........................... | 260/248 X |
| 3,824,229 | 7/1974 | Szekeres et al.................. | 260/248 |

*Primary Examiner*—John M. Ford

[57] ABSTRACT

Process for preparing 2',3',5'-tri-0-acetyl-6-azauridine having the following formula

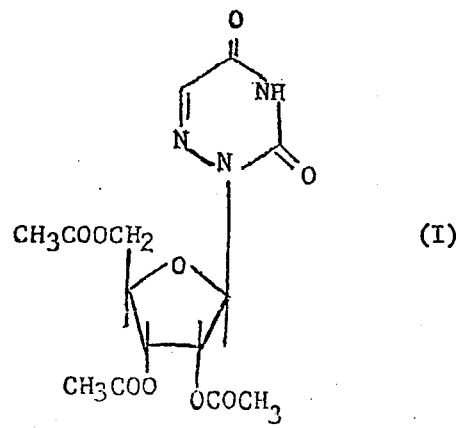

(I)

which comprises reacting a crude anomeric mixture of methyl D-ribofuranosides having the formula

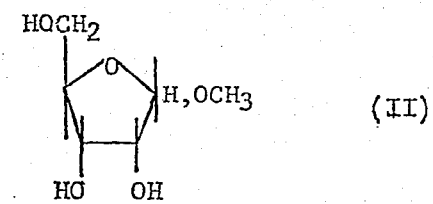

(II)

with anhydrous hydrogen chloride or anhydrous hydrogen bromide in the presence of acetic anhydride and acetic acid to thereby form the corresponding 2,3-,5-tri-0-acetyl-D-ribofuranosyl halide having the formula

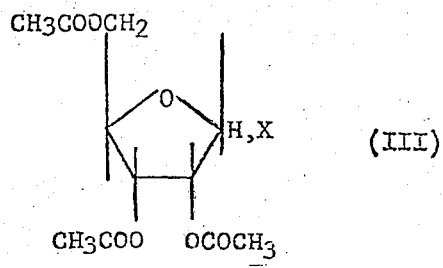

(III)

wherein X is chloro or bromo, reacting the halide of formula III with 3,5-bis-trimethylsilyloxy-1,2,4-triazine having the following formula

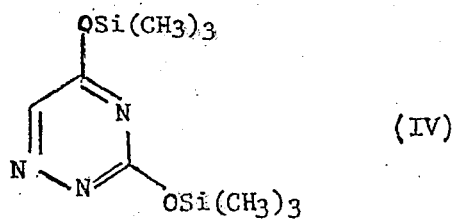

(IV)

in the presence of an inert solvent and a mercuric halide and recovering the 2',3',5'-tri-0-acetyl-6-azauridine.

5 Claims, No Drawings

PROCESS FOR PREPARING 2′,3′,5′-TRI-0-ACETYL-6-AZAURIDINE

The invention relates to a process for preparing 2′,3′,5′-tri-O-acetyl-6-azauridine. This compound has been used effectively in treatment of psoriasis and of certain diseases of viral origin. The 2′,3′,5′-tri-O-acetyl-6-azauridine prepared conforms to the formula

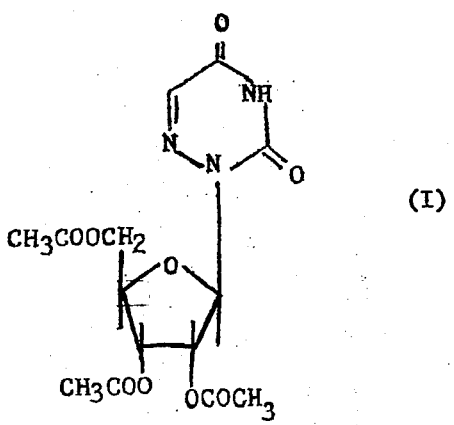

(I)

The compound of the above formula may, in accordance with the invention, may be prepared by treating a mixture of anomeric methyl-D-ribofuranosides with anhydrous hydrogen chloride or bromide in a medium comprising acetic anhydride and glacial acetic acid, to thereby form the corresponding 2′,3′,5′-tri-O-acetyl-D-ribofuranosyl halide which is in a second step condensed with 3,5-bis-trimethylsilyloxy-1,2,4-triazine in the presence of an inert solvent and of a mercuric halide as catalyst. The reaction of the 2,3,5-tri-O-acetyl-D-ribofuranosyl halide with 3,5-bis-trimethyl-silyloxy-1,2,4-triazine is advantageously carried out at room temperature in the presence of anhydrous 1,2-dichloroethane or anhydrous acetonitrile and 0.1–0.5 mol equivalents of mercuric bromide.

6-Azauridine or 6-azauracil riboside is a pyrimidine anti-metabolite finding a wide application in biochemical and pharmacological research as well as in clinical practice. It is used in the form of the per-orally active triacetate having the formula I as set out above in the treatment of psoriasis and of certain diseases of viral origin.

The compound of formula I may be prepared either by acetylation of 6-azauridine (Czechoslovak Pat. No. 111,202) or directly by the reaction of 2,3,5-tri-O-acetyl-D-ribofuranosyl halide with a dialkoxy- or alkoxyalkylthio-1,2,4-triazine and the subsequent dealkylation of the alkoxy group or the selective hydrolysis of the alkylthio group U.S. Application Ser. No. 306,838, filed Nov. 15, 1972, now U.S. Pat. No. 3,869,446.

The advantage of the method based on the direct synthesis of the triacetylribofuranosyl halide lies in the elimination of the necessity of relying on the relatively expensive production of the free 6-azauridine. The triacetylribofuranosyl halide required for use in this process is prepared by reaction of a hydrogen halide with 1,2,3,5-tetra-O-acetyl-β-D-ribofuranose. The latter tetraacetate compound is obtained by acetolysis of the relatively expensive purine ribonucleoside or more advantageously, from the less expensive D-ribose (see Guthrie R. D. and Smith S. C., Chem. & Ind. (London) 547 (1968) ). This latter preparation of the crystalline tetraacetyl-D-ribofuranose is economically unsatisfactory, the yield amounts to only about 50%. However, the use of a crude non-crystalline tetra-acetyl-D-ribofuranose results in low yields of 6-azauridine triacetate. Another drawback of the above-mentioned direct syntheses consists in the necessity for removing the alkoxy or alkylthio group from the condensation product of the triacetylribofuranosyl halide with the dialkoxy-triazine or alkoxyalkylthio-1,2,4-triazine. The removal of such groups by the dealkylation of the alkoxy group or by the selective hydrolysis of the alkylthio group is accompanied by a considerable loss of material due to the sensitivity of the acetyl groups.

It is an object of the present invention to provide a process for preparing 2′,3′,5′-tri-O-acetyl-6-azauridine avoiding the disadvantages associated with the known processes.

It is another object of the invention to provide a direct process for preparing 2′,3′,5′-tri-O-acetyl-6-azauridine.

Still another object of the invention is to provide such a process associated with short reaction times and producing the desired product in high yields.

These and other objects and advantages are attained in accordance with the invention as will become apparent from a consideration of the following disclosure.

In accordance with the invention it has now surprisingly been found that the triacetylribofuranosyl halide can be obtained by the direct reaction of a hydrogen halide with a mixture of anomeric methyl D-ribofuranosides which can be obtained substantially quantitatively with very short reaction times by the known procedures from D-ribose, in a mixture of acetic anhydride and glacial acetic acid. The time consuming preparation of the crystalline tetraacetylribofuranose is thus superfluous and thereby the process for making the triacetylribofuranosyl halide is markedly shortened. Another advantage in accordance with the invention consists in the use for the second step of the known 3,5-bis-trimethylsilyloxy-1,2,4-triazine instead of 3,5-dialkoxy-1,2,4-triazine as the reactant for condensation wit the triacetylribofuranosyl halide. The trimethylsilyloxy group is removed under mild conditions in the presence of water during the work-up of the crude reaction mixture and the final product is thereby directly obtained.

3,5-Bis-trimethylsilyloxy-1,2,4-triazine is prepared from 6-azauracil, i.e., 1,2,4-triazine-3,5(2H,4H)-dione, either by raction with trimethylchlorosilane and triethylamine in refluxing benzene or by reacting also under reflux of hexamethyldisilazane. The former procedure has been found to provide 3,5-bis-trimethylsilyloxy-1,2,4-triazine of an inferior quality and in a low yield while a highly pure product is obtained in an almost quantitative yield by the latter procedure; the disadvantage of this latter procedure, however, consists in the high price of hexamethyldisilazane.

In accordance with the invention, it has further been discovered that the silylation of 6-azauracil with trimethylchlorosilane and triethylamine affords an almost quantitative yield of the required 3,5-bis-trimethylsilyloxy-1,2,4-triazine in pure form when the reaction is carried out in the higher-boiling toluene and when a longer reaction period of time is used.

The preparation of the analogous 2′,3′,5′-tri-O-benzoyl-6-azauridine has been reported in the literature (see Abstracts of Papers N-18, 21st IUPAC International Congress in Prague, September, 1967; Rev. Roumaine Chim. 13, 365 (1968); Angew.Chem. 82, 449 (1970)). Under such conditions as therein described, however, the required 2',3',5'-tri-O-acetyl-6-azauridine is obtained only in low yields and may be isolated only by chromatography. The low yields are due to the formation of the position isomers and disubstituted derivatives or may be ascribed to side reactions of the halogenose with the catalysts employed in the process such as mercuric oxide or mercuric acetate. Even in the absence of any catalyst and with the use of acetonitrile as solvent, the reaction does not yield a pure product and the yield of 6-azauridine triacetate is furthermore quite low.

As has been established by additional detailed investigations of the condensation of 2,3,5-tri-O-acetyl-D-ribofuranosyl halide with 3,5-bis-trimethylsilyloxy-1,2,4-triazine, the required 2',3',5'-tri-O-acetyl-6-azauridine of formula I is obtained in a surprisingly high yield when the reaction is conducted in the presence of a mercuric halide at room temperature and in an inert solvent such as 1,2-dichloroethane or acetonitrile.

According to the process of the invention, 2',3',5'-tri-O-acetyl-6-azauridine having formula I is prepared by treating a mixture of anomeric methyl D-ribofuranosides having the following formula

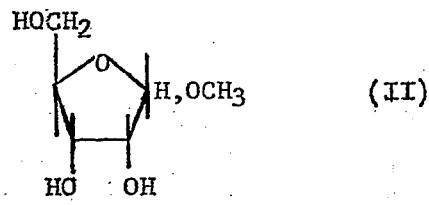

with anhydrous hydrogen chloride or anhydrous hydrogen bromide in a medium consisting of acetic anhydride and glacial acetic acid, thereby forming a 2,3,5-tri-O-acetyl-D-ribofuranosyl halide having the following formula

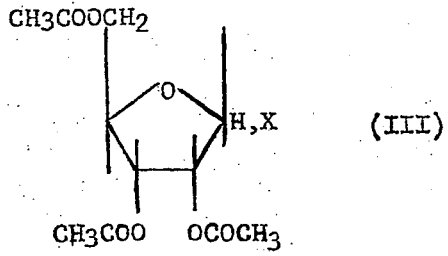

wherein X designates chloro or bromo, and condensing the compound III with 3,5-bis-trimethylsilyloxy-1,2,4-triazine having the following formula

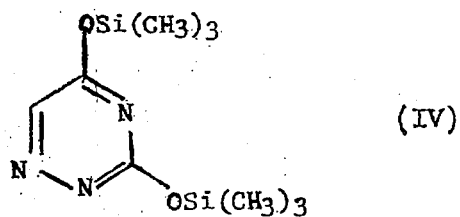

in the presence of an inert solvent and in the additional presence of a mercuric halide.

The reaction of the hydrogen halide with the mixture of anomeric methyl D-ribofuranoside corresponding to formula II is performed in an excess of a mixture of acetic anhydride and acetic acid present in a ratio of 3:2 in such mixture. Other ratios of acetic anhydride to acetic acid may also be used, but the mixture resulting after completion of the reaction must necessarily contain an at least a small excess of the unreacted acetic anhydride. It is also advantageous to carry out the initial stage of the reaction, exothermal acetylation of the free hydroxylic groups, with cooling and then to complete the reaction at room temperature. The anhydrous hydrogen halide may be introduced into the mixture of anomeric methyld D-ribofuranosides in the gaseous form or may be added in the form of a concentrated solution in glacial acetic acid to a mixture of anomeric methyl D-ribofuranosides and acetic anhydride alone or to a mixture of acetic anhydride and glacial acetic acid. The halogenoses are obtained from the reaction mixture without any loss being occasioned by the coevaporation of the excess acetic anhydride and acetic acid with anhydrous toluene under decreased pressure and they can then be used in the subsequent step without any purification.

Condensation of the halogenoses corresponding to formula III with the triazine having formula IV is preferably carried out at room temperature. The reactants are used in an equimolar ratio or the triazine of formula IV may be used in a small excess.

As inert solvents, there may be used anhydrous acetonitrile, 1,2-dichloroethane, dichloromethane, chloroform or any other aprotic solvents.

As catalysts, mercuric halides are used. In the case of the chlorohalogenose, good results are obtained with mercuric bromide; mercuric iodide was equally satisfactory while mercuric chloride proved somewhat less efficient. In the case of the bromohalogenose, also mercuric chloride proved to be a satisfactory catalyst. With the more reactive bromohalogenose, high yields are obtained in the presence of 0.1 mol equivalent of mercuric bromide while the less reactive chlorohalogenose requires 0.3–0.5 mol equivalent of mercuric bromide. A further increase of the mercuric bromide-halogenose ratio does not affect the yield but the reaction is faster.

Preparation of 2',3',5'-tri-O-acetyl-6-azauridine

Example 1

A solution of a mixture of anomeric methyl D-ribofuranosides (the mixture was prepared in the convention manner (supra) from 7.5 g of D-ribose) in a mixture of acetic anhydride (30 ml) and acetic acid (20 ml) was saturated for 2 to 3 hours with dry gaseous hydrogen chloride under cooling with ice-cold water and exclusion of atmospheric moisture. At the beginning of the reaction (first 20 to 30 minutes), the hydrogen chloride was introduced very slowly; thereafter the rate of introduction was increased until saturation was completed. The solution (calcium chloride tube) was then kept at room temperature for 20 to 24 hours, thereafter diluted with dry toluene and evaporated under decreased pressure at 35°–40°C (bath temperature). The residual syrup was coevaporated with three 20 ml portions of dry toluene. The thusly obtained 2,3,5-tri-O-acetyl-D-ribofuranosyl chloride was dissolved in dry 1,2-dichloroethane (50 ml) and the solution successively treated with 3,5-bis-trimethylsilyloxy-1,2,4-triazine (14 g) and mercuric bromide (9 g). The resultant mixture was subjected to thorough stirring in order to yield a substantially clear solution which was kept at room temperature overnight under exclusion of atmospheric moisture. This dark solution was thereafter evaporated under decreased pressure and the residue dissolved in chilled chloroform. The solution which was obtained was thoroughly washed with two 70 ml portions of 30% aqueous potassium iodide containing a small amount (0.1 g) of sodium thiosulfate. The combined aqueous layers were extracted with three 20 ml portions of chloroform.

The chloroform solutions were combined, dried over anhydrous sodium sulfate, and evaporated under decreased pressure. The residue which was formed was chromatographed on a column of silica gel (100 g; partially deactivated by the addition of 10% of water), 20 ml fractions were taken off, the course of elution was followed by thin-layer chromatography. The column was successively eluted with 500 ml of 9:1 benzene-ethyl acetate, 500 ml of 8:2 benzene-ethyl acetate, and 500 ml of 1:1 benzene-ethyl acetate. The 2′,3′,5′-tri-O-acetyl-6-azauridine compound-containing fractions were combined and evaporated under decreased pressure. The residual syrup was dissolved in a mixture of ether (50 ml) and benzene (5 ml), the solution seeded and maintained under occasional stirring for 2 hours at room temperature and then in an ice-box overnight. The crystals which formed were collected with suction, washed with cold ether, and air-dried. The mother liquors were evaporated and the residue subjected to an analogous crystallization to provide an additional small crop of the product. The overall yield amounted to 12.45 g (67% referred to D-ribose) and had a melting point of 98°–100°C.

Example 2

To a mixture of anomeric methyl D-ribofuranosides (prepared in the conventional manner (supra) from 7.5 g of D-ribose) and acetic anhydride (30 ml) there was added in dropwise fashion with stirring and ice-cooling a 40% solution of hydrogen bromide in glacial acetic acid; the first drops were introduced very slowly (approximately one drop per 30–60 seconds). The remaining solution was quickly dropped into the mixture. The resulting solution was kept at room temperature for 1–2 hours under exclusion of atmospheric moisture, then diluted with dry toluene (100 ml), and evaporated under decreased pressure at 35°–40°C (bath temperature). The residual syrup was coevaporated with three 50 ml portions of dry toluene. The thusly obtained 2,3,5-tri-O-acetyl-D-ribofuranosyl bromide was dissolved in dry 1,2-dichloroethane (50 ml) and the solution treated with 3,5-bis-trimethylsilyloxy-1,2,4-triazine (14 g) and mercuric bromide (5.4 g). The entire mixture was made homogeneous, kept at room temperature overnight, and processed analogously to the procedure described in Example 1. The overall yield amounted to 10.75 g (58%, referred to D-ribose) of 2′,3′,5′-tri-O-acetyl-6-azauridine, m.p. 98°–100°C.

Example 3

A solution of 1,2,3,5-tetra-O-acetyl-β-D-ribofuranose (obtained in the usual manner from 6.0 g of D-ribose) in a mixture of dry 1,2-dichloroethane (20 ml) and acetyl chloride (0.5g) was saturated for one hour with dry hydrogen chloride gas under cooling with ice-cold water and exclusion of atmospheric moisture. The solution was then kept at room temperature overnight and evaporated under decreased pressure at 35°–40°C (bath temperature). The residual syrup was coevaporated with three 20 ml portions of dry toluene. The thusly obtained 2,3,5-tri-O-acetyl-D-ribofuranosyl chloride was processed analogously to the procedure of Example 1. The overall yield amounted to 6.25 g (84%, referred to tetraacetyl-D-ribose; 42%, referred to D-ribose) of 2′,3′,5′-tri-O-acetyl-6-azauridine, m.p. 98°–100°C.

We claim:

1. A process for producing 2′,3′,5′-tri-O-acetyl-6-azauridine having the formula:

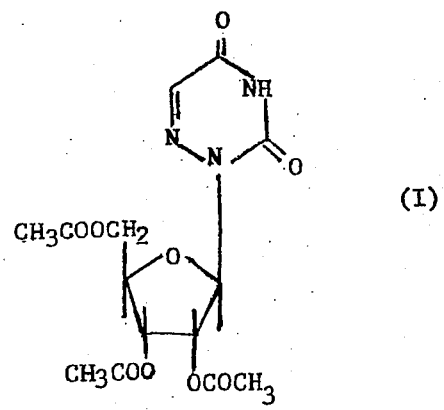

which consists of the steps of reacting a crude anomeric mixture of methyl D-ribofuranosides having the formula

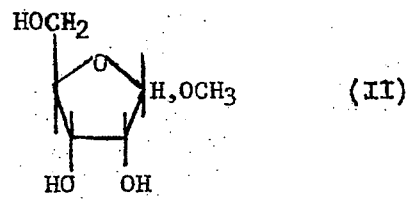

with anhydrous hydrogen chloride or anhydrous hydrogen bromide in the presence of acetic anhydride and acetic acid to thereby form the corresponding 2,3,5-tri-O-acetyl-D-ribofuranosyl halide having the formula

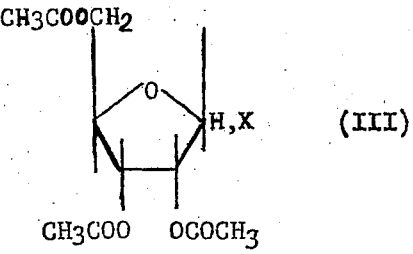

wherein X is chloro or bromo, and thereafter reacting the halide of formula III with 3,5-bis-trimethylsilyloxy-1,2,4-triazine having the formula

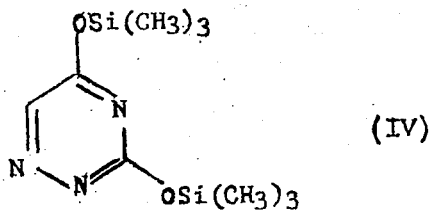

in the presence of an inert solvent of a mercuric halide and recovering the 2′,3′,5′-tri-O-acetyl-6-azauridine.

2. The process according to claim 1, wherein the reaction of the compounds of formula III with the compound of formula IV is conducted at room temperature in the presence of anhydrous acetonitrile and of 0.1 – 0.5 mol equivalents of mercuric bromide.

3. The process according to claim 1 wherein the inert solvent is selected from the group consisting of acetonitrile, 1,2-dichlorethane, dichlormethane and chloroform.

4. The process according to claim 1 wherein said mercuric halide is selected from the group consisting of mercuric chloride, mercuric bromide and mercuric iodide.

5. The process according to claim 1 wherein said hydrogen chloride or hydrogen bromide is used in gaseous form.

* * * * *